United States Patent
King et al.

(10) Patent No.: US 6,413,531 B2
(45) Date of Patent: Jul. 2, 2002

(54) POTENTIATION OF BIOCIDE ACTIVITY USING A DIETHANOLAMIDE

(75) Inventors: Vanja M. King; Marilyn S. Whittemore; Xiangdon Zhou, all of Memphis, TN (US)

(73) Assignee: Buckman Laboratories International, Inc., Memphis, TN (US)

(*) Notice: Subject to any disclaimer, the term of this patent is extended or adjusted under 35 U.S.C. 154(b) by 0 days.

(21) Appl. No.: 09/861,559

(22) Filed: May 22, 2001

Related U.S. Application Data

(62) Division of application No. 09/031,515, filed on Feb. 27, 1998, now Pat. No. 6,235,299.

(51) Int. Cl.$^7$ .................. A01N 25/00; A61K 31/425; A61K 31/415; A61K 31/185; A61K 31/16
(52) U.S. Cl. .................. 424/405; 514/370; 514/385; 514/553; 514/613
(58) Field of Search .................. 424/405; 514/365–370, 514/385, 553, 613

(56) References Cited

U.S. PATENT DOCUMENTS

| | | | |
|---|---|---|---|
| 3,520,976 A | 7/1970 | Buckman et al. | 424/270 |
| 3,629,454 A | 12/1971 | Barr et al. | 424/320 |
| 3,923,870 A | 12/1975 | Singer | 260/482 C |
| 4,293,559 A | 10/1981 | Buckman et al. | 424/270 |
| 4,479,961 A | 10/1984 | Martin | 424/270 |
| 4,595,691 A | 6/1986 | LaMarre et al. | 514/367 |
| 4,839,373 A | 6/1989 | Ito et al. | 514/367 |
| 4,866,081 A | 9/1989 | Ito et al. | 514/367 |
| 4,944,892 A | 7/1990 | Leathers et al. | 252/92 |
| 4,945,109 A | 7/1990 | Rayudu | 514/478 |
| 5,219,875 A | 6/1993 | Sherba et al. | 514/373 |
| 5,277,156 A | 1/1994 | Wiese | 424/70 |
| 5,279,875 A | 1/1994 | Juszak et al. | 428/42 |
| 5,328,926 A | 7/1994 | Oppong | 514/372 |
| 5,413,795 A | 5/1995 | Lee et al. | 424/489 |
| 5,622,911 A | 4/1997 | Hasebe et al. | 504/116 |
| 5,746,814 A | 5/1998 | Malhotra et al. | 106/18 |

FOREIGN PATENT DOCUMENTS

| | | |
|---|---|---|
| EP | 0 356 264 | 2/1990 |
| EP | 0 651 049 | 5/1995 |
| JP | 50117923 | 9/1975 |
| WO | 91/12721 | 9/1991 |
| WO | 97/16066 | 5/1997 |

OTHER PUBLICATIONS

CAPLUS Abstract, AN 1992:189611, Hidaka et al. 1992.*
Nemcova et al, Chemical Abstracts, "Corrosion inhibitor for aqueous heat exchange media", 1984, Document No. 100:144797.
International Search Report, dated Jun. 23, 1999, in International Application No. PCT/US99/03943.

* cited by examiner

*Primary Examiner*—Russell Travers
*Assistant Examiner*—Shengjun Wang
(74) *Attorney, Agent, or Firm*—Morgan, Lewis & Bockius LLP

(57) ABSTRACT

A method for increasing the effectiveness of a biocide is described. In the method, at least one biocide and at least one diethanolamide are applied to a substrate or aqueous system subject to the growth of microorganisms. The diethanolamide is applied in an amount effective to increase the biocidal activity of the biocide. Biocidal compositions are described where the biocide and the diethanolamide are present in a combined amount effective to control the growth of at least one microorganism. Methods for controlling the growth of microorganisms on various substrates and in various aqueous systems are also described. The combination of the biocide and the diethanolamide is particularly useful as a biocide in the leather industry, the lumber industry, the papermaking industry, the textile industry, the agricultural industry, and the coating industry, as well as in industrial process waters.

7 Claims, No Drawings

POTENTIATION OF BIOCIDE ACTIVITY USING A DIETHANOLAMIDE

This is a divisional of application Ser. No. 09/031,515 filed on Feb. 27, 1998, now U.S. Pat. No. 6,235,299.

FIELD OF THE INVENTION

The invention relates to compositions and methods for controlling the growth of microorganisms on a variety of substrates and in aqueous systems. More particularly, the invention relates to a combination of at least one biocide with at least one diethanolamide where the diethanolamide potentiates the biocide's biocidal effect.

BACKGROUND OF THE INVENTION

A large variety of commercial, industrial, agricultural, and wood materials or products are subject to microbiological attack or degradation which reduces or destroys their economic value. Examples of such materials or products include surface coatings, lumber, seeds, plants, leather and plastics. The various temperatures at which such materials or products are manufactured, stored, or used as well as their intrinsic characteristics make them susceptible to growth, attack, and degradation by common microorganisms such as algae, fungi, yeasts, and bacteria. These microorganisms may be introduced during manufacturing or other industrial process, by exposure to air, tanks, pipes, equipment, and humans. They can also be introduced while using a material or product, for example, by multiple openings and reclosures of packages or from stirring or removing material with contaminated objects.

Aqueous systems are also highly subject to microbiological growth, attack, and degradation. These aqueous systems may be fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, process water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiological growth and thus attack and degradation.

Microbiological degradation of aqueous systems may manifest itself as a variety of problems, such as loss of viscosity, gas formation, objectionable odors, decreased pH, emulsion breaking, color change, and gelling. Additionally, microbiological deterioration of aqueous systems can cause fouling of the related water-handling system, which may include cooling towers, pumps, heat exchangers, and pipelines, heating systems, scrubbing systems, and other similar systems.

Another objectionable phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms. Slime reduces yields in production and causes plugging, bulking, and other problems in industrial water systems.

Various chemicals known as biocides have been used to prevent microbiological deterioration of industrial systems, raw materials, and products. Examples of such biocides include:

TCMTB formulations, containing the fungicide 2-(thiocyanomethylthio)-benzothiazole (TCMTB), which are known in the art and have often been used to control or prevent biological fouling, including biofilm and slime formation, in aqueous systems. TCMTB has been used for industrial microorganism control for over 20 years. TCMTB is known to be useful in controlling bacteria and fungi in various aqueous systems and is commercially available from Buckman Laboratories, Inc., Memphis, Tenn., under the tradenames BUSAN® 30WB and BUSAN® 1030 as a 30% active ingredient. The preparation and use of 2-(thiocyanomethyl-thio)-benzothiazole as a microbicide and a preservative is described in U.S. Pat. Nos. 3,520,976, 4,293,559, 4,866,081, 4,595,691, 4,944,892, 4,839,373, and 4,479,961 give examples of microbicidal properties of 2-(thiocyanomethylthio)benzothiazole. U.S. Pat. No. 5,413,795 describes compositions having TCMTB adsorbed onto a solid carrier. The disclosures of all of these patents are incorporated herein by reference.

Kathon: a two component microbiocide mixture of 5-chloro-2-methyl-4-isothiazolin-3-one (CMI) and 2-methyl-4-isothiazolin-3-one (MI). Kathon is a broad spectrum microbiocide used in the pulp and paper industry. Kathon is also recommended to control bacteria and fungi in water-based paper coatings and coating components. Kathon is available from Rohm and Haas, Philadelphia Pa. and as BUSAN® 1078 from Buckman Laboratories, Memphis, Tenn. BUSAN® 1078 is contains 1.15% by weight of CMI and 0.35% by weight of MI as active ingredients. CMI and MI have the following chemical structures:

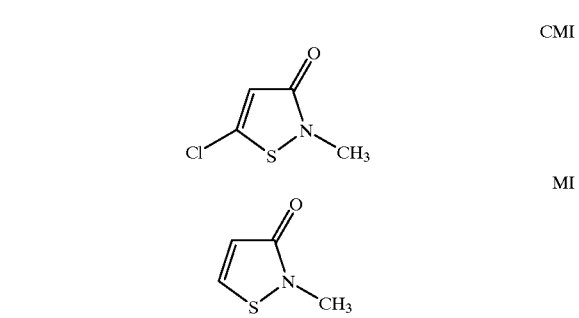

Bronopol: 2-bromo-2-nitropropane-1,3-diol. Bronopol is available as MYACIDE® from Angus Chemical Company, Northbrook, Ill. Bronopol is used in water treatment, oil production fluids, waste injection wells, and with pulp and paper. The chemical formula of bronopol is:

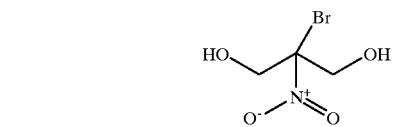

IPBC: Iodopropargyl butyl carbamate. IPBC can be obtained from Troy Chemical, Newark, N.J. IPBC is an effective fungicide, particularly in surface coating compositions, such as paint formulations. IPBC is disclosed in U.S. Pat. Nos. 3,923,870 and 5,219,875. IPBC has the following chemical formula:

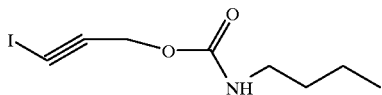

IPC: Iodopropargyl carbamate. IPC, an effective microbiocide in aqueous systems and on numerous substrates, is disclosed in U.S. Pat. Nos. 4,945,109 and 5,328,926. The chemical formula of IPC is:

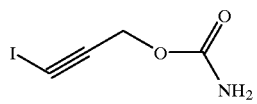

DBNPA: 2,2-Dibromo-3-nitrilopropionamide. DBNPA is available from Dow Chemical Company, Midland, Mich. and Buckman Laboratories, Memphis, Tenn. as the product BUSAN® 94. DBNPA is a broad spectrum bactericide having particular use to control slime in the pulp and paper industry. BUSAN® 94 contains 20% by weight of DBNPA as its active ingredient. DBNPA has the chemical structure:

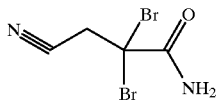

Tribromophenol: 2,4,6-Tribromophenol. Tribromophenol is an antifungal agent available from Great Lakes Chemical, West Lafayette, Ind. under the trade name GREAT LAKES PH-73. The chemical formula of tribromophenol is:

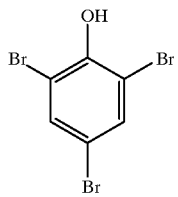

BIT: 1,2-benzisothiazoline-3-one. 1,2-Benzisothiazoline-3-one is a biocide useful for a variety of aqueous systems, such as metalworking fluids, paint, adhesives, starch-based-products, cellulose ether solutions, resin and rubber emulsions. 1,2-benzisothiazoline-3-one is available from ICI Specialty Chemicals, Melbourne, Australia as the product PROXEL GXL-20, an aqueous solution of dipropylene glycol 20% by weight of 1,2-benzisothiazoline-3-one as the active ingredient. 1,2-Benzisothiazoline-3-one has the following chemical structure:

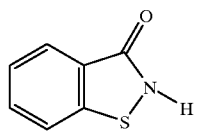

Propiconazole, also known as (RS)-1- 2-[(2,4-dichlorophenyl)-2-propyl-1,3-dioxalan-2ylmethyl]-1H-1,2, 4-triazole, is one commercial biocide which has been shown to have a reasonably good toxicological profile and biocidal activity. Propiconazole is commercially available from Buckman Laboratories, Inc., Memphis, Tenn., for example, as a formulation containing about 24% actives under the tradename BUSAN® 1292. Propiconazole has the following chemical structure:

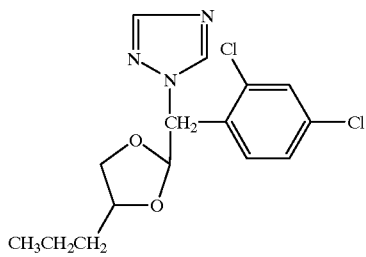

Other biocides include potassium N-hydroxymethyl-N-methyl thiocarbamate, a 30% active ingredient in BUSAN® 52 product and 2-bromo-4'-hydroxyacetophenone, a 30% active ingredient in BUSAN® 90. These products are available from Buckman Laboratories, Memphis, Tenn.

Despite the existence of such biocides, industry is constantly seeking more cost-effective technology which offers equal or better protection at lower cost and lower concentration. The concentration of conventional biocides and the corresponding treatment costs for such use, can be relatively high. Important factors in the search for cost-effective fungicides include the duration of biocidal effect, reduced environmental impact, the ease of use and the effectiveness of the biocide per unit weight.

SUMMARY OF THE INVENTION

In view of industry's search for more cost effective biocides, the invention offers an improvement over current products or practices.

The invention relates to a method to increase the effectiveness of a biocide. This method applies at least one biocide and at least one diethanolamide to a substrate or aqueous system subject to the growth of microorganisms. The diethanolamide is applied in an amount effective to increase the biocidal activity of the biocide. The combination of the biocide with a diethanolamide achieves superior biocidal activity at lower concentrations and lower cost than the biocide alone against microbiological attack or degradation such as discussed above.

One embodiment of the invention provides a biocidal composition. The composition contains (a) at least one biocide and (b) at least one fatty acid diethanolamide. In the composition, the biocide (a) and the diethanolamide (b) are present in a combined amount effective to control the growth of at least one microorganism.

Another embodiment of the invention provides a method for controlling the growth of a microorganism on a substrate.

This method contacts a substrate susceptible to the growth of microorganisms with at least one biocide and a diethanolamide. The biocide and diethanolamide are present in a combined amount effective to control the growth of at least one microorganism on the substrate.

The combination of biocide and diethanolamide according to the invention may be used for controlling the growth of microorganisms in aqueous systems. Thus, another embodiment of the invention provides a method for controlling the growth of microorganisms in an aqueous system capable of supporting growth of a microorganism. This method treats the aqueous system with at least one biocide and at least one diethanolamide above. The biocide and the diethanolamide are present in a combined amount effective to control the growth of at least one microorganism in the aqueous system.

The biocide and diethanolamide combination of the invention is useful in preventing the microbiological attack, degradation, or deterioration of various types of raw materials and products such as leather, textiles, pulp, paper and paperboard, coatings, lumber, as well as agricultural products such as seeds and crops. Advantageously, the combination may be used in various industrial processes used to prepare or manufacture these products. Accordingly, additional embodiments of the invention employ the combination to control the growth of microorganisms on or in such industrial products, raw materials or processes.

The foregoing and other features and advantages of the invention will be made more apparent from the following detailed description and preferred embodiments.

DETAILED DESCRIPTION OF THE INVENTION

The invention relates to a method to increase the effectiveness of a biocide. This method applies at least one biocide and at least one diethanolamide to a substrate or aqueous system subject to the growth of microorganisms. The diethanolamide is applied in an amount effective to increase the biocidal activity of the biocide.

According to the invention, the combination of a biocide and a diethanolamide demonstrates an unexpected, enhanced biocidal effect. That is, the combination of a biocide and a diethanolamide achieves superior biocidal activity at lower biocide concentrations as compared to the biocidal capability of the biocide alone, although the amount of diethanolamide used has no biocidal effect itself. Thus, the diethanolamide potentiates the biocidal activity of the biocide. Such a superior effect presents a distinct economic advantage and increases an individual biocide's effectiveness per unit weight.

According to the invention, a diethanolamide may be used to increase the effectiveness of any biocide or a mixture of biocides. Preferred biocides include potassium N-hydroxymethyl-N-methyl thiocarbamate, 2-thiocyanomethylthiobenzothiazole, propiconazole, 2-bromo-4'-hydroxyacetophenone, sodium 2-mercaptobenzothiazole and mixtures thereof. The diethanolamide may be used with and in the same manner as the particular biocide is used. Preferably, one or more diethanolamides are incorporated into the formulation of the biocide.

In one embodiment, the invention relates to a biocidal composition comprising at least one biocide and at least one diethanolamide. The biocide and the diethanolamide are present in a combined amount effective to control the growth of at least one microorganism. Mixtures of diethanolamides may also be used.

A general synthesis of diethanolamides mixes a 1:1 molar ratio of diethanolamine with a fatty acid or mixture of fatty acids. The mixture is then heated at a reflux under vacuum for several hours and water is removed. If a mixture of acids is used, an averaged molecular weight is calculated based on the ratio of individual acids in the mixture. Completion of the reaction can be monitored by IR analysis or free fatty acid content.

Fatty acids are carboxylic acids derived from or contained in an animal or vegetable fat or oil. Fatty acids are composed of a chain of alkyl groups containing from about 4 to about 22 carbon atoms (usually even numbered) and have a terminal carboxylic acid group. Fatty acids may be straight or branched, saturated or unsaturated and even aromatic. Fatty acids which may be used in the preparation of the diethanolamide include, but are not limited to, butyric acid, lauric acid, decanoic acid, undecylenic acid, palmitic acid, stearic acid, palmitoleic acid, oleic acid, isooleic acid, linoleic acid, linolenic acid, and phenyl stearic acid. Fatty acids employed in this invention preferably have long alkyl chains in the $C_{12}$-$C_{22}$ range, with $C_{16}$-$C_{20}$ being preferred. Unsaturated fatty acids such as oleic, isooleic, linoleic, and linolenic are preferred.

Mixtures of fatty acids may also be used in the preparation of mixtures of diethanolamide. For example, tall oil fatty acids, palm oil fatty acids, and coconut oil fatty acids are mixtures of fatty acids which may be used to prepare a mixture of diethanolamides. Tall oil fatty acid (TOFA), which is predominantly a mixture of oleic acid (~45 wt. %) and linoleic acid (~36 wt. %) and other fatty acids, is available from Arizona Chemical Company, Panama City, Fla. Another mixture of fatty acids is sold under the trade name Century MO-5 by Union Camp Chemical Company of Jacksonville, Fla. The Century MO-5 fatty acid mixture contains about 46 wt. % isooleic acid, 37 wt. % oleic acid and 17 wt. % of saturated fatty acids such as palmitic acid and stearic acid. Mixtures of fatty acids represent a preferred embodiment of the invention.

Depending on the application, biocidal compositions according to the invention may be prepared in various forms known in the art. For example, the composition may be prepared in liquid form as an aqueous solution, dispersion, emulsion, or suspension, a dispersion or suspension in a non-solvent, or as a solution by dissolving the biocide and the diethanolamide in a solvent or combination of solvents. Suitable solvents include, but are not limited to, methyl ethers of glycols, M-pyrol, or petroleum distillates. The biocidal composition may be prepared as a concentrate for dilution prior to its intended use. Common additives such as surfactants, emulsifiers, dispersants, and the like may be used as known in the art to increase the solubility of the biocide or diethanolamide in a liquid composition or system, such as an aqueous composition or system. In many cases, the biocidal composition of the invention may be solubilized by simple agitation.

Biocidal compositions of the invention may also be prepared in solid form, for example as a powder or tablet, using means known in the art. In a preferred method of preparation, a liquid product containing the biocide is deposited on a carrier such as diatomaceous earth or kaolin and mixed with a diethanolamide in the form of a liquid or solution to form a powder or tablet.

The biocide and the diethanolamide may be combined in a single composition. Alternatively, the biocide and the diethanolamide may be employed as separate components such that the combined amount for the intended use is effective to control the growth of at least one microorganism.

As discussed above, the diethanolamide potentiates the biocidal effect of the biocide. Thus, combining a diethanolamide with a biocide provides superior biocidal activity to control the growth of microorganisms as compared to the biocidal capability of the biocide alone. Although the diethanolamide may exhibit biocidal activity at concentrations above certain threshold levels, the diethanolamide is not biocidally effective at the concentrations used.

According to the invention, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time. The combination of biocide and diethanolamide described here can, in many cases, reduce the total microbiological count to undetectable limits and maintain the count at that level for a significant period of time. Accordingly, the combination may be used to preserve a substrate or system.

The effective amount or percentage of the combination of a biocide and a diethanolamide necessary to achieve the desired result will vary somewhat depending on the substrate or aqueous system to be protected, the conditions for microbial growth, the particular biocide, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 0.2%. With aqueous systems, an effective amount may range from about 0.5 to about 5000 parts per million, more preferably from about 5 to about 1000 parts per million of the aqueous system, and most preferably from, about 10 to about 25 parts per million. Similar amounts effectively control slime formation. For slime control, effective amounts preferably range from about 1 to about 200 parts per million, and more preferably, from about 1 to about 25 parts per million of the aqueous system, and in some cases as low as 0.5 ppm.

In a preferred embodiment, combinations of a biocide and a diethanolamide are those combinations having a weight ratio of biocide to diethanolamide from about 99:1 to about 1:99. More preferably the weight ratio is from about 60:10 to about 10:60, and most preferably, from about 50:50 to about 25:75. The weight ratio may vary depending on the biocide, the intended use, the microorganism encountered as well as the particular material, product, or system to which the combination according to the invention is applied.

The combination of a biocide and a diethanolamide may be applied in a variety of industrial uses and processes for microorganism control. The combination may be used in place of and in the same manner as other biocides traditionally used in the particular industry. As discussed above, such industries include, but are not limited to, the leather industry, the lumber industry, the papermaking industry, the textile industry, the agricultural industry, and the coating industry. The combination of a biocide and a diethanolamide may also be used with aqueous systems such as those previously discussed which are subject to microbiological attack and degradation. The problems caused by microbiological attack and deterioration in these various applications has been described above. The use of the combination of a biocide and a diethanolamide according to the invention to control the growth of microorganisms in particular exemplary applications is described below.

The invention also relates to a method for controlling the growth of microorganisms on various substrates. The method comprises the step of contacting a substrate susceptible to microbiological growth or attack with a biocide and a diethanolamide, as described above. The biocide and diethanolamide are present in a combined amount effective to control the growth of at least one microorganism on the substrate. Preferably, the method may be used to eliminate or prevent substantially all microbiological growth on the substrate. As discussed above, the biocide and the diethanolamide may be applied together or as separate compositions. Preferred applications of this general method are discussed below.

In the leather industry, the combination of a biocide and a diethanolamide may be used to control the growth of microorganisms on a hide during a tanning process. To achieve this control, the hide is contacted with a combined amount of a biocide and a diethanolamide effective to control the growth of at least one microorganism on the hide. The combination of the biocide and the diethanolamide may be used in the tanning process in similar amounts and manner similar to that used to apply other biocides used in the tanning industry. The type of hide may be any type of hide or skin that is tanned, for example cowhide, snake skin, alligator skin, sheep skin, and the like. The amount used, to some extent, will depend on the degree of microbiological resistance required and may be readily determined by one skilled in the art.

A typical tanning process comprises a number of stages, including, but not limited to, a pickling stage, a chrome-tanning stage, a vegetable-tanning stage, a post-tan washing stage, a retanning stage, a dyeing stage, and a fatliquoring stage. The combination of a biocide and a diethanolamide may be used during all process stages in the tanning process in addition to those stages where a known microbiological problem is occurring. In each stage, the combination of a biocide and a diethanolamide may be a component of the appropriate tanning liquor applied to the hide undergoing tanning.

Incorporating the biocide and a diethanolamide in a tanning liquor protects the hide from microbiological deterioration during the tanning process. Preferably, the combination is uniformly dispersed, e.g., under agitation, into an appropriate liquor to be used in a tanning process. Typical tanning liquors include, for example, a pickling liquor, a chrome-tanning liquor, a vegetable-tanning liquor, a post-tan washing liquor, a retanning liquor, a dye liquor, and a fatliquor. This method of application ensures that the combination applied to the hides protects against microbiological attack, deterioration, or other microbiological degradation.

In a somewhat analogous nature, the combination of the invention may also be employed to control the growth of microorganisms on a textile substrate in a textile manufacturing process. Contacting the textile substrate with a combination of a biocide and a diethanolamide according to the invention effectively controls the growth of a microorganism on the textile substrate. In a textile process, the combination may be used in similar amounts and a manner similar to other biocides commonly used in such processes. As one of ordinary skill would appreciate, particular amounts generally depend on the textile substrate and the degree of microbiological resistance required.

The step of contacting the textile substrate with the combination of a biocide and a diethanolamide may be accomplished using means known in the textile art. To control microbiological growth, a textile process generally dips the textile substrate into a bath containing a biocide, alone or with other chemicals used to treat the textile substrate. Alternatively, the textile substrate may be sprayed with a formulation containing a biocide. In the bath or the spray, the combination of biocide and diethanolamide according to the invention are present in a combined amount effective to control the growth of at least one microorganism on the textile substrate. Preferably, the bath and the spray are aqueous-based compositions.

To preserve the value of its raw materials and products, the lumber industry also must control the growth of microorganisms in order to prevent microbiological degradation of lumber. The combination of a biocide and a diethanolamide according to the invention is effective to control the growth of microorganisms on lumber.

The combination of a biocide and a diethanolamide may be used to protect the lumber in similar amounts and a similar manner employed for other biocides used in the lumber industry. Contacting lumber with an effective amount of the combination may be accomplished, for example, by spraying the lumber with an aqueous formulation containing the combination of a biocide and a diethanolamide, by dipping the lumber into a dip bath containing the combination, or other means known in the art. Dipping the lumber in an aqueous bath is preferred.

The biocide and the diethanolamide are preferably uniformly dispersed in a bath (for example, by agitation) prior to the dipping of the lumber into the bath. In general, the lumber is dipped into the bath, raised, allowed to drip dry, and then air dried. The dip time will depend, as is known in the art, on a variety of factors such as the biocide, the degree of microbiological resistance desired, the moisture content of the lumber, type and density of the wood, etc. Pressure may be applied to promote penetration of the combination into the lumber being treated. Applying a vacuum to the upper surface of the lumber may also be used to degas the lumber and promote increased wetting of the lumber by a bath containing the biocidal combination.

The combination of a biocide and a diethanolamide according to the invention also has uses in the agricultural industry. To control the growth of microorganisms on a seed or plant, the seed or plant may be contacted with a biocide and a diethanolamide in a combined amount effective to control the growth of at least one microorganism on the seed or plant. This contacting step may be accomplished using means and amounts known in the agricultural industry for other biocides. For example, the seed or plant may be sprayed with an aqueous formulation containing the combination of biocide and diethanolamide, or dipped into a bath containing the combination. After being sprayed or dipped, the seed or plant is generally dried by means known in the art such as drip drying, heated drying, or air drying. For plants or crops, the combination may also be applied using a soil drench. Soil drenching is particularly advantageous when the microorganisms of concern inhabit the soil surrounding the plant.

Yet another aspect of the invention is a method for controlling the growth of microorganisms in an aqueous system capable of supporting such growth. The aqueous system is treated with a biocide and a diethanolamide such that the biocide and diethanolamide are present in a combined amount effective to control the growth of at least one microorganism in the aqueous system. This includes controlling, and preferably preventing, slime formation in the aqueous system.

Examples of various aqueous systems include, but are not limited to, latexes, surfactants, dispersants, stabilizers, thickeners, adhesives, starches, waxes, proteins, emulsifying agents, cellulose products, aqueous emulsions, aqueous detergents, coating compositions, paint compositions, alum compositions, and resins formulated in aqueous solutions, emulsions or suspensions. The combination may also be employed in aqueous systems used in industrial processes such as metal working fluids, cooling waters (both intake cooling water and effluent cooling water), and waste waters including waste waters or sanitation waters undergoing treatment of the waste in the water, e.g., sewage treatment.

As with the other uses discussed above, the combination of a biocide and a diethanolamide according to the invention may be used in the same amounts and in the same manner as biocides traditionally used in these various aqueous systems. The combination not only protects the aqueous system prior to use or when stored, but in many cases protects the aqueous system when in use or in appropriate applications even after the aqueous system has dried. When used in a paint formulation for example, the combination not only protects the paint in the can, but also the paint film after being applied to a substrate.

Another embodiment of the invention is a method for controlling the growth of microorganisms on paper or in a papermaking process, e.g., in a pulp or paper slurry and on a finished paper product such as paper board. The paper, pulp, or slurry is contacted with a biocide and a diethanolamide in a combined amount effective to control the growth of at least one microorganism on the paper, the pulp or in a slurry. The contacting step is accomplished using means and amounts known in the papermaking art.

According to this aspect of the invention, for example, a forming web on a papermaking machine (or a wet-lap pulp) may be contacted with the combination of a biocide and a diethanolamide by spraying an aqueous dispersion containing the biocide and diethanolamide onto the pulp after the pulp leaves the presses in a papermaking process. Or, the biocide and the diethanolamide may be incorporated into a bath used at the wet or size press and the web contacted by nipping the web to incorporate the combination into the web with any other agents applied at the press. Alternatively, the pulp may be contacted by mixing the biocide and diethanolamide into the pulp/white water mixture, preferably prior to the pulp reaching the formation wire.

When treating paper (which includes paperboard and other cellulosic products or substrates), the biocide and diethanolamide may be added into pulp slurries in the headbox, in the substrate forming solution, or in the white water system to treat the water system itself or for incorporation into the body of the paper. Alternatively, as with other known biocides, the combination of a biocide and a diethanolamide according to the invention may be mixed into a coating used to coat the finished paper.

The activity of the combinations described above has been confirmed using standard laboratory techniques as discussed below. In many cases, the diethanolamide potentiates the biocidal affect of the particular biocide. The following examples are intended to illustrate, not limit, the invention.

EXAMPLES

Preparation of N,N-Diethanol Tall Oil Fatty Acid Amide 1.24 moles of tall oil fatty acid (350 grams, 282 grams/mole) were added with 1.24 mole diethanolamine (130 grams, 105.14 grams/mole) to a three neck round bottom flask equipped with a stirrer. The mixture was heated at reflux under vacuum for several hours. Aliquots were removed to detect formation of amide peak by IR to monitor completion of the reaction.

Potentiating Effect of Diethanolamides

The following materials and procedure were used to determine the potentiating effect of a diethanolamide with various biocides.

Materials

1. Microorganisms
   (1) Pseudomonas aeruginosa ("Ps. aeruginosa") ATCC 15442 (a bacterium)
   (2) Aspergillus niger ("A. niger") ATCC 9642 (a fungus).
2. Biocides
   (1) potassium N-hydroxymethyl-N-methyl thiocarbamate, a 30% active ingredient in BUSAN® 52 product;
   (2) 2-thiocyanomethylthiobenzothiazole as BUSAN® 1030;
   (3) 24% active propiconazole as BUSAN®) 1292; and
   (4) 2-bromo-4'-hydroxyacetophenone as BUSAN® 90.
3. Diethanolamides
   (1) N,N-diethanol tall oil fatty amide; and
   (2) diethanolamide of Century MO-5.
4. Growth Media
   (1) Antibacterial Test:
   NaCl, 8.0 g; glucose, 1.0 g; tryptone, 1.0 g; DI water, 1.0 L.
   (2) Antifungal Test:

| | | |
|---|---|---|
| $KH_2PO_4$, 0.7 g; | $MgSO_4 7H_2O$, 0.7 g; | $MnSO_4 7H_2O$, 1.0 mg; |
| NaCl, 5.0 mg; | $FeSO_4 7H_2O$, 2.0 mg; | $ZnSO_4 7H_2O$, 2.0 mg; |
| $NH_4NO_3$, 1.0 g; | Glucose, 10.0 g; | DI Water, 1.0 L. |

Procedure 5 ml of growth medium were suspended in test tubes, and the culture medium was autoclaved at 121° C. for 20 min. Biocide stock aqueous solutions were added in each tube to give the desired biocide-diethanolamide concentrations in parts per million. No biocide was added to the control tubes. All tubes were inoculated by adding 0.1 ml of inoculum to give a bacterial concentration of about $10^6$ cells/ml ($10^6$ spores/ml for fungal test). After each addition, the tubes were shaken vigorously to mix the contents thoroughly. All inoculated tubes were placed at 37° C. for antibacterial test and at 28° C. for antifungal test. Bacterial growth was checked after 5–7 days and fungal growth was checked after 10–14 days.

The MIC of each biocide and diethanolamide acting alone and in combination was determined on a growth-no-growth basis. Tables 1–16 present both the lowest concentrations of each biocide and diethanolamide separately for which there was no growth, and the lowest concentration of biocide in combination with diethanolamide for which there was no growth. A plus (+) sign represents the presence of fugal or bacterial mat and a minus (−) sign represents the absence of fungal or bacterial mat. The only tables which demonstrate a neutral effect are Tables 2 and 4 where both diethanolamide of Century MO-5 and N,N-diethanol tall oil fatty amide had a neutral effect against Ps. aeruginosa. This is due to the fact that propiconazole does not have any antibacterial activity within the concentration range tested, i.e., up to 2000 ppm.

TABLE 1

Combination of BUSAN® 1292 with diethanolamide of Century MO-5 against A. niger

| BUSAN® 1292 (ppm) | Diethanolamide (ppm) | Growth | BUSAN® 1292 (ppm) | Diethanolamide (ppm) | Growth |
|---|---|---|---|---|---|
| 5 | 0 | + | 20 | 10 | + |
| 10 | 0 | + | 20 | 20 | + |
| 20 | 0 | + | 20 | 50 | + |
| 40 | 0 | + | 20 | 100 | + |
| 60 | 0 | + | 20 | 200 | + |
| 80 | 0 | − | 20 | 500 | + |
| 0 | 10 | + | 40 | 10 | + |
| 0 | 20 | + | 40 | 20 | + |
| 0 | 50 | + | 40 | 50 | + |
| 0 | 100 | + | 40 | 100 | + |
| 0 | 200 | + | 40 | 200 | − |
| 0 | 500 | + | 40 | 500 | − |
| 5 | 10 | + | 60 | 10 | − |
| 5 | 20 | + | 60 | 20 | − |
| 5 | 50 | + | 60 | 50 | − |
| 5 | 100 | + | 60 | 100 | − |
| 5 | 200 | + | 60 | 200 | − |
| 5 | 500 | + | 60 | 500 | − |
| 10 | 10 | + | 80 | 10 | − |
| 10 | 20 | + | 80 | 20 | − |
| 10 | 50 | + | 80 | 50 | − |
| 10 | 100 | + | 80 | 100 | − |
| 10 | 200 | + | 80 | 200 | − |
| 10 | 500 | + | 80 | 500 | − |

TABLE 2

Combination of BUSAN® 1292 with diethanolamide of Century MO-5 against Ps. aeruginosa

| BUSAN® 1292 (ppm) | Diethanolamide (ppm) | Growth | BUSAN® 1292 (ppm) | Diethanolamide (ppm) | Growth |
|---|---|---|---|---|---|
| 100 | 0 | + | 500 | 10 | + |
| 200 | 0 | + | 500 | 20 | + |
| 500 | 0 | + | 500 | 50 | + |
| 800 | 0 | + | 500 | 100 | + |
| 1000 | 0 | + | 500 | 200 | + |
| 2000 | 0 | + | 500 | 500 | + |
| 0 | 10 | + | 800 | 10 | + |
| 0 | 20 | + | 800 | 20 | + |
| 0 | 50 | + | 800 | 50 | + |
| 0 | 100 | + | 800 | 100 | + |
| 0 | 200 | + | 800 | 200 | + |
| 0 | 500 | + | 800 | 500 | + |
| 100 | 10 | + | 1000 | 10 | + |
| 100 | 20 | + | 1000 | 20 | + |
| 100 | 50 | + | 1000 | 50 | + |
| 100 | 100 | + | 1000 | 100 | + |
| 100 | 200 | + | 1000 | 200 | + |
| 100 | 500 | + | 1000 | 500 | + |
| 200 | 10 | + | 2000 | 10 | + |
| 200 | 20 | + | 2000 | 20 | + |
| 200 | 50 | + | 2000 | 50 | + |
| 200 | 100 | + | 2000 | 100 | + |
| 200 | 200 | + | 2000 | 200 | + |
| 200 | 500 | + | 2000 | 500 | + |

TABLE 3

Combination of BUSAN ® 1292 with N,N-diethanol tall oil fatty amide against *A. niger*

| BUSAN ® 1292 (ppm) | Diethanol-amide (ppm) | Growth | BUSAN ® 1292 (ppm) | Diethanol-amide (ppm) | Growth |
|---|---|---|---|---|---|
| 5 | 0 | + | 20 | 10 | + |
| 10 | 0 | + | 20 | 20 | + |
| 20 | 0 | + | 20 | 50 | + |
| 40 | 0 | + | 20 | 100 | + |
| 60 | 0 | + | 20 | 200 | + |
| 80 | 0 | − | 20 | 500 | + |
| 0 | 10 | + | 40 | 10 | − |
| 0 | 20 | + | 40 | 20 | − |
| 0 | 50 | + | 40 | 50 | + |
| 0 | 100 | + | 40 | 100 | + |
| 0 | 200 | + | 40 | 200 | + |
| 0 | 500 | + | 40 | 500 | − |
| 5 | 10 | + | 60 | 10 | − |
| 5 | 20 | + | 60 | 20 | − |
| 5 | 50 | + | 60 | 50 | − |
| 5 | 100 | + | 60 | 100 | − |
| 5 | 200 | + | 60 | 200 | − |
| 5 | 500 | + | 60 | 500 | − |
| 10 | 10 | + | 80 | 10 | − |
| 10 | 20 | + | 80 | 20 | − |
| 10 | 50 | + | 80 | 50 | − |
| 10 | 100 | + | 80 | 100 | − |
| 10 | 200 | + | 80 | 200 | − |
| 10 | 500 | + | 80 | 500 | − |

TABLE 4

Combination of BUSAN ® 1292 with N,N-diethanol tall oil fatty amide against *Ps. aeruginosa*

| BUSAN ® 1292 (ppm) | Diethanol-amide (ppm) | Growth | BUSAN ® 1292 (ppm) | Diethanol-amide (ppm) | Growth |
|---|---|---|---|---|---|
| 100 | 0 | + | 500 | 10 | + |
| 200 | 0 | + | 500 | 20 | + |
| 500 | 0 | + | 500 | 50 | + |
| 800 | 0 | + | 500 | 100 | + |
| 1000 | 0 | + | 500 | 200 | + |
| 2000 | 0 | + | 500 | 500 | + |
| 0 | 10 | + | 800 | 10 | + |
| 0 | 20 | + | 800 | 20 | + |
| 0 | 50 | + | 800 | 50 | + |
| 0 | 100 | + | 800 | 100 | + |
| 0 | 200 | + | 800 | 200 | + |
| 0 | 500 | + | 800 | 500 | + |
| 100 | 10 | + | 1000 | 10 | + |
| 100 | 20 | + | 1000 | 20 | + |
| 100 | 50 | + | 1000 | 50 | + |
| 100 | 100 | + | 1000 | 100 | + |
| 100 | 200 | + | 1000 | 200 | + |
| 100 | 500 | + | 1000 | 500 | − |
| 200 | 10 | + | 2000 | 10 | − |
| 200 | 20 | + | 2000 | 20 | − |
| 200 | 50 | + | 2000 | 50 | − |
| 200 | 100 | + | 2000 | 100 | + |
| 200 | 200 | + | 2000 | 200 | + |
| 200 | 500 | + | 2000 | 500 | + |

TABLE 5

Combination of BUSAN ® 1030 with diethanolamide of Century MO-5 against *A. niger*

| BUSAN ® 1030 (ppm) | Diethanol-amide (ppm) | Growth | BUSAN ® 1030 (ppm) | Diethanol-amide (ppm) | Growth |
|---|---|---|---|---|---|
| 0.25 | 0 | + | 0.75 | 10 | − |
| 0.50 | 0 | + | 0.75 | 20 | − |
| 0.75 | 0 | − | 0.75 | 50 | − |
| 1 | 0 | − | 0.75 | 100 | − |
| 2 | 0 | − | 0.75 | 200 | − |
|  |  |  | 0.75 | 500 | − |
| 0 | 10 | + | 1 | 10 | − |
| 0 | 20 | + | 1 | 20 | − |
| 0 | 50 | + | 1 | 50 | − |
| 0 | 100 | + | 1 | 100 | − |
| 0 | 200 | + | 1 | 200 | − |
| 0 | 500 | + | 1 | 500 | − |
| 0.25 | 10 | + | 2 | 10 | − |
| 0.25 | 20 | + | 2 | 20 | − |
| 0.25 | 50 | + | 2 | 50 | − |
| 0.25 | 100 | + | 2 | 100 | − |
| 0.25 | 200 | + | 2 | 200 | − |
| 0.25 | 500 | + | 2 | 500 | − |
| 0.50 | 10 | − |  |  |  |
| 0.50 | 20 | − |  |  |  |
| 0.50 | 50 | − |  |  |  |
| 0.50 | 100 | − |  |  |  |
| 0.50 | 200 | − |  |  |  |
| 0.50 | 500 | − |  |  |  |

TABLE 6

Combination of BUSAN ® 1030 with diethanolamide of Century MO-5 against *Ps. aeruginosa*

| BUSAN ® 1030 (ppm) | Diethanol-amide (ppm) | Growth | BUSAN ® 1030 (ppm) | Diethanol-amide (ppm) | Growth |
|---|---|---|---|---|---|
| 10 | 0 | + | 40 | 10 | + |
| 20 | 0 | + | 40 | 20 | − |
| 40 | 0 | + | 40 | 50 | − |
| 80 | 0 | − | 40 | 100 | − |
| 160 | 0 | − | 40 | 200 | + |
|  |  |  | 40 | 500 | + |
| 0 | 10 | + | 80 | 10 | − |
| 0 | 20 | + | 80 | 20 | − |
| 0 | 50 | + | 80 | 50 | − |
| 0 | 100 | + | 80 | 100 | − |
| 0 | 200 | + | 80 | 200 | − |
| 0 | 500 | + | 80 | 500 | − |
| 10 | 10 | + | 160 | 10 | − |
| 10 | 20 | + | 160 | 20 | − |
| 10 | 50 | + | 160 | 50 | − |
| 10 | 100 | + | 160 | 100 | − |
| 10 | 200 | + | 160 | 200 | − |
| 10 | 500 | + | 160 | 500 | − |
| 20 | 10 | + |  |  |  |
| 20 | 20 | + |  |  |  |
| 20 | 50 | − |  |  |  |
| 20 | 100 | − |  |  |  |
| 20 | 200 | − |  |  |  |
| 20 | 500 | + |  |  |  |

TABLE 7

Combination of BUSAN ® 1030 with N,N-diethanol tall oil fatty amide against *A. niger*

| BUSAN ® 1030 (ppm) | Diethanol-amide (ppm) | Growth | BUSAN ® 1030 (ppm) | Diethanol-amide (ppm) | Growth |
|---|---|---|---|---|---|
| 0.20 | 0 | + | 0.5 | 1 | + |
| 0.50 | 0 | + | 0.5 | 5 | + |
| 1 | 0 | − | 0.5 | 10 | − |
| 2 | 0 | − | 0.5 | 25 | − |
| 4 | 0 | − | 0.5 | 50 | − |
|   |   |   | 0.5 | 100 | + |
| 0 | 1 | + | 1 | 1 | − |
| 0 | 5 | + | 1 | 5 | − |
| 0 | 10 | + | 1 | 10 | − |
| 0 | 25 | + | 1 | 25 | − |
| 0 | 50 | + | 1 | 50 | − |
| 0 | 100 | + | 1 | 100 | − |
| 0.2 | 1 | + | 2 | 1 | − |
| 0.2 | 5 | + | 2 | 5 | − |
| 0.2 | 10 | + | 2 | 10 | − |
| 0.2 | 25 | + | 2 | 25 | − |
| 0.2 | 50 | + | 2 | 50 | − |
| 0.2 | 100 | + | 2 | 100 | − |

TABLE 8

Combination of BUSAN ® 1030 with N,N-diethanol tall oil fatty amide against *Ps. aruginosa*

| BUSAN ® 1030 (ppm) | Diethanol-amide (ppm) | Growth | BUSAN ® 1030 (ppm) | Diethanol-amide (ppm) | Growth |
|---|---|---|---|---|---|
| 10 | 0 | + | 40 | 1 | + |
| 20 | 0 | + | 40 | 5 | + |
| 40 | 0 | + | 40 | 10 | − |
| 80 | 0 | − | 40 | 25 | − |
| 160 | 0 | − | 40 | 50 | − |
|   |   |   | 40 | 100 | − |
| 0 | 1 | + | 80 | 1 | − |
| 0 | 5 | + | 80 | 5 | − |
| 0 | 10 | + | 80 | 10 | − |
| 0 | 25 | + | 80 | 25 | − |
| 0 | 50 | + | 80 | 50 | − |
| 0 | 100 | + | 80 | 100 | − |
| 10 | 1 | + | 160 | 1 | − |
| 10 | 5 | + | 160 | 5 | − |
| 10 | 10 | + | 160 | 10 | − |
| 10 | 25 | + | 160 | 25 | − |
| 10 | 50 | + | 160 | 50 | − |
| 10 | 100 | + | 160 | 100 | − |
| 20 | 1 | + |   |   |   |
| 20 | 5 | + |   |   |   |
| 20 | 10 | + |   |   |   |
| 20 | 25 | + |   |   |   |
| 20 | 50 | + |   |   |   |
| 20 | 100 | + |   |   |   |

TABLE 9

Combination of BUSAN ® 52 with diethanolamide of Century MO-S against *A. niger*

| BUSAN ® 52 (ppm) | Diethanol-amide (ppm) | Growth | BUSAN ® 52 (ppm) | Diethanol-amide (ppm) | Growth |
|---|---|---|---|---|---|
| 5 | 0 | + | 20 | 10 | + |
| 10 | 0 | + | 20 | 20 | + |
| 20 | 0 | + | 20 | 50 | − |
| 50 | 0 | − | 20 | 100 | − |
| 100 | 0 | − | 20 | 200 | − |

TABLE 9-continued

Combination of BUSAN ® 52 with diethanolamide of Century MO-S against *A. niger*

| BUSAN ® 52 (ppm) | Diethanol-amide (ppm) | Growth | BUSAN ® 52 (ppm) | Diethanol-amide (ppm) | Growth |
|---|---|---|---|---|---|
| 200 | 0 | − | 20 | 500 | − |
| 0 | 10 | + | 50 | 10 | − |
| 0 | 20 | + | 50 | 20 | − |
| 0 | 50 | + | 50 | 50 | − |
| 0 | 100 | + | 50 | 100 | − |
| 0 | 200 | + | 50 | 200 | − |
| 0 | 500 | + | 50 | 500 | − |
| 5 | 10 | + | 100 | 10 | − |
| 5 | 20 | + | 100 | 20 | − |
| 5 | 50 | + | 100 | 50 | − |
| 5 | 100 | + | 100 | 100 | − |
| 5 | 200 | + | 100 | 200 | − |
| 5 | 500 | + | 100 | 500 | − |
| 10 | 10 | + | 200 | 10 | − |
| 10 | 20 | + | 200 | 20 | − |
| 10 | 50 | + | 200 | 50 | − |
| 10 | 100 | + | 200 | 100 | − |
| 10 | 200 | + | 200 | 200 | − |
| 10 | 500 | + | 200 | 500 | − |

TABLE 10

Combination of BUSAN ® 52 with diethanolamide of Century MO-5 against *Ps. aeruginosa*

| BUSAN ® 52 (ppm) | Diethanol-amide (ppm) | Growth | BUSAN ® 52 (ppm) | Diethanol-amide (ppm) | Growth |
|---|---|---|---|---|---|
| 10 | 0 | + | 50 | 10 | + |
| 20 | 0 | + | 50 | 20 | + |
| 50 | 0 | + | 50 | 50 | − |
| 100 | 0 | + | 50 | 100 | − |
| 200 | 0 | − | 50 | 200 | + |
| 400 | 0 | − | 50 | 500 | + |
| 0 | 10 | + | 100 | 10 | + |
| 0 | 20 | + | 100 | 20 | − |
| 0 | 50 | + | 100 | 50 | − |
| 0 | 100 | + | 100 | 100 | − |
| 0 | 200 | + | 100 | 200 | − |
| 0 | 500 | + | 100 | 500 | + |
| 10 | 10 | + | 200 | 10 | − |
| 10 | 20 | + | 200 | 20 | − |
| 10 | 50 | + | 200 | 50 | − |
| 10 | 100 | + | 200 | 100 | − |
| 10 | 200 | + | 200 | 200 | − |
| 10 | 500 | + | 200 | 500 | − |
| 20 | 10 | + | 400 | 10 | − |
| 20 | 20 | + | 400 | 20 | − |
| 20 | 50 | + | 400 | 50 | − |
| 20 | 100 | + | 400 | 100 | − |
| 20 | 200 | + | 400 | 200 | − |
| 20 | 500 | + | 400 | 500 | − |

TABLE 11

Combination of BUSAN ® 52 with N,N-diethanol tall oil fatty amide against *A. niger*

| BUSAN ® 52 (ppm) | Diethanol-amide (ppm) | Growth | BUSAN ® 52 (ppm) | Diethanol-amide (ppm) | Growth |
|---|---|---|---|---|---|
| 5 | 0 | + | 20 | 10 | − |
| 10 | 0 | + | 20 | 20 | − |
| 20 | 0 | + | 20 | 50 | − |
| 50 | 0 | − | 20 | 100 | − |

TABLE 11-continued

Combination of BUSAN ® 52 with N,N-diethanol tall oil fatty amide against *A. niger*

| BUSAN ® 52 (ppm) | Diethanol-amide (ppm) | Growth | BUSAN ® 52 (ppm) | Diethanol-amide (ppm) | Growth |
|---|---|---|---|---|---|
| 100 | 0 | − | 20 | 200 | − |
| 200 | 0 | − | 20 | 500 | + |
| 0 | 10 | + | 50 | 10 | − |
| 0 | 20 | + | 50 | 20 | − |
| 0 | 50 | + | 50 | 50 | − |
| 0 | 100 | + | 50 | 100 | − |
| 0 | 200 | + | 50 | 200 | − |
| 0 | 500 | + | 50 | 500 | − |
| 5 | 10 | + | 100 | 10 | − |
| 5 | 20 | + | 100 | 20 | − |
| 5 | 50 | + | 100 | 50 | − |
| 5 | 100 | + | 100 | 100 | − |
| 5 | 200 | + | 100 | 200 | − |
| 5 | 500 | + | 100 | 500 | − |
| 10 | 10 | + | 200 | 10 | − |
| 10 | 20 | + | 200 | 20 | − |
| 10 | 50 | + | 200 | 50 | − |
| 10 | 100 | + | 200 | 100 | − |
| 10 | 200 | + | 200 | 200 | − |
| 10 | 500 | + | 200 | 500 | − |

TABLE 12

Combination of BUSAN ® 52 with N,N-diethanol tall oil fatty amide against *Ps. aeruginosa*

| BUSAN ® 52 (ppm) | Diethanol-amide (ppm) | Growth | BUSAN ® 52 (ppm) | Diethanol-amide (ppm) | Growth |
|---|---|---|---|---|---|
| 10 | 0 | + | 50 | 10 | + |
| 20 | 0 | + | 50 | 20 | + |
| 50 | 0 | + | 50 | 50 | + |
| 100 | 0 | + | 50 | 100 | + |
| 200 | 0 | − | 50 | 200 | + |
| 400 | 0 | − | 50 | 500 | + |
| 0 | 10 | + | 100 | 10 | − |
| 0 | 20 | + | 100 | 20 | − |
| 0 | 50 | + | 100 | 50 | − |
| 0 | 100 | + | 100 | 100 | − |
| 0 | 200 | + | 100 | 200 | − |
| 0 | 500 | + | 100 | 500 | − |
| 10 | 10 | + | 200 | 10 | − |
| 10 | 20 | + | 200 | 20 | − |
| 10 | 50 | + | 200 | 50 | − |
| 10 | 100 | + | 200 | 100 | − |
| 10 | 200 | + | 200 | 200 | − |
| 10 | 500 | + | 200 | 500 | − |
| 20 | 10 | + | 400 | 10 | − |
| 20 | 20 | + | 400 | 20 | − |
| 20 | 50 | + | 400 | 50 | − |
| 20 | 100 | + | 400 | 100 | − |
| 20 | 200 | + | 400 | 200 | − |
| 20 | 500 | + | 400 | 500 | − |

TABLE 13

Combination of BUSAN ® 90 with diethanolamide of Century MO-5 against *A. niger*

| BUSAN ® 90 (ppm) | Diethanol-amide (ppm) | Growth | BUSAN ® 90 (ppm) | Diethanol-amide (ppm) | Growth |
|---|---|---|---|---|---|
| 2.5 | 0 | + | 10 | 10 | + |
| 5 | 0 | + | 10 | 20 | + |
| 10 | 0 | + | 10 | 50 | − |

TABLE 13-continued

Combination of BUSAN ® 90 with diethanolamide of Century MO-5 against *A. niger*

| BUSAN ® 90 (ppm) | Diethanol-amide (ppm) | Growth | BUSAN ® 90 (ppm) | Diethanol-amide (ppm) | Growth |
|---|---|---|---|---|---|
| 20 | 0 | − | 10 | 100 | − |
| 40 | 0 | − | 10 | 200 | − |
| 80 | 0 | − | 10 | 500 | + |
| 0 | 10 | + | 20 | 10 | − |
| 0 | 20 | + | 20 | 20 | − |
| 0 | 50 | + | 20 | 50 | − |
| 0 | 100 | + | 20 | 100 | − |
| 0 | 200 | + | 20 | 200 | − |
| 0 | 500 | + | 20 | 500 | − |
| 2.5 | 10 | + | 40 | 10 | − |
| 2.5 | 20 | + | 40 | 20 | − |
| 2.5 | 50 | + | 40 | 50 | − |
| 2.5 | 100 | + | 40 | 100 | − |
| 2.5 | 200 | + | 40 | 200 | − |
| 2.5 | 500 | + | 40 | 500 | − |
| 5 | 10 | + | 80 | 10 | − |
| 5 | 20 | − | 80 | 20 | − |
| 5 | 50 | − | 80 | 50 | − |
| 5 | 100 | + | 80 | 100 | − |
| 5 | 200 | + | 80 | 200 | − |
| 5 | 500 | + | 80 | 500 | − |

TABLE 14

Combination of BUSAN ® 90 with diethanolamide of Century MO-5 against *Ps. aeruginosa*

| BUSAN ® 90 (ppm) | Diethanol-amide (ppm) | Growth | BUSAN ® 90 (ppm) | Diethanol-amide (ppm) | Growth |
|---|---|---|---|---|---|
| 5 | 0 | + | 20 | 10 | + |
| 10 | 0 | + | 20 | 20 | + |
| 20 | 0 | + | 20 | 50 | + |
| 40 | 0 | + | 20 | 100 | + |
| 80 | 0 | − | 20 | 200 | + |
| 160 | 0 | − | 20 | 500 | + |
| 0 | 10 | + | 40 | 10 | + |
| 0 | 20 | + | 40 | 20 | + |
| 0 | 50 | + | 40 | 50 | + |
| 0 | 100 | + | 40 | 100 | + |
| 0 | 200 | + | 40 | 200 | − |
| 0 | 500 | + | 40 | 500 | − |
| 5 | 10 | + | 80 | 10 | − |
| 5 | 20 | + | 80 | 20 | − |
| 5 | 50 | + | 80 | 50 | − |
| 5 | 100 | + | 80 | 100 | − |
| 5 | 200 | + | 80 | 200 | − |
| 5 | 500 | + | 80 | 500 | − |
| 10 | 10 | + | 160 | 10 | − |
| 10 | 20 | + | 160 | 20 | − |
| 10 | 50 | + | 160 | 50 | − |
| 10 | 100 | + | 160 | 100 | − |
| 10 | 200 | + | 160 | 200 | − |
| 10 | 500 | + | 160 | 500 | − |

TABLE 15

Combination of BUSAN ® 90 with N,N-diethanol tall oil fatty amide against *A. niger*

| BUSAN ® 90 (ppm) | Diethanol-amide (ppm) | Growth | BUSAN ® 52 (ppm) | Diethanol-amide (ppm) | Growth |
|---|---|---|---|---|---|
| 2.5 | 0 | + | 10 | 1 | + |
| 5 | 0 | + | 10 | 5 | + |

TABLE 15-continued

Combination of BUSAN ® 90 with N,N-diethanol tall oil fatty amide against *A. niger*

| BUSAN ® 90 (ppm) | Diethanol-amide (ppm) | Growth | BUSAN ® 52 (ppm) | Diethanol-amide (ppm) | Growth |
|---|---|---|---|---|---|
| 10 | 0 | + | 10 | 10 | + |
| 20 | 0 | − | 10 | 20 | − |
| 40 | 0 | − | 10 | 50 | − |
| 80 | 0 | − | 10 | 100 | − |
| 0 | 1 | + | 20 | 1 | − |
| 0 | 5 | + | 20 | 5 | − |
| 0 | 10 | + | 20 | 10 | − |
| 0 | 20 | + | 20 | 20 | − |
| 0 | 50 | + | 20 | 50 | − |
| 0 | 100 | + | 20 | 100 | − |
| 2.5 | 1 | + | 40 | 1 | − |
| 2.5 | 5 | + | 40 | 5 | − |
| 2.5 | 10 | + | 40 | 10 | − |
| 2.5 | 20 | + | 40 | 20 | − |
| 2.5 | 50 | + | 40 | 50 | − |
| 2.5 | 100 | + | 40 | 100 | − |
| 5 | 1 | + | 80 | 1 | − |
| 5 | 5 | + | 80 | 5 | − |
| 5 | 10 | + | 80 | 10 | − |
| 5 | 20 | + | 80 | 20 | − |
| 5 | 50 | + | 80 | 50 | − |
| 5 | 100 | + | 80 | 100 | − |

TABLE 16

Combination of BUSAN ® 90 with N,N-diethanol tall oil fatty amide against *Ps. aeruginosa*

| BUSAN ® 90 (ppm) | Diethanol-amide (ppm) | Growth | BUSAN ® 90 (ppm) | Diethanol-amide (ppm) | Growth |
|---|---|---|---|---|---|
| 5 | 0 | + | 20 | 1 | + |
| 10 | 0 | + | 20 | 5 | + |
| 20 | 0 | + | 20 | 10 | + |
| 40 | 0 | + | 20 | 25 | + |
| 80 | 0 | − | 20 | 50 | + |
| 160 | 0 | − | 20 | 100 | + |
| 0 | 1 | + | 40 | 1 | + |
| 0 | 5 | + | 40 | 5 | + |
| 0 | 10 | + | 40 | 10 | − |
| 0 | 25 | + | 40 | 25 | − |
| 0 | 50 | + | 40 | 50 | − |
| 0 | 100 | + | 40 | 100 | − |
| 5 | 1 | + | 80 | 1 | − |
| 5 | 5 | + | 80 | 5 | − |
| 5 | 10 | + | 80 | 10 | − |
| 5 | 25 | + | 80 | 25 | − |
| 5 | 50 | + | 80 | 50 | − |
| 5 | 100 | + | 80 | 100 | − |
| 10 | 1 | + | 160 | 1 | − |
| 10 | 5 | + | 160 | 5 | − |
| 10 | 10 | + | 160 | 10 | − |
| 10 | 25 | + | 160 | 25 | − |
| 10 | 50 | + | 160 | 50 | − |
| 10 | 100 | + | 160 | 100 | − |

The claimed invention is:

1. A biocidal composition comprising:

(a) at least one biocide selected from the group consisting of potassium N-hydroxymethyl-N-methyl thiocarbamate, 2-thiocyanomethylthiobenzothiazole, propiconazole, 2-bromo-4'-hydroxyacetophenone, sodium 2-mercaptobenzothiazole and mixtures thereof, and (b) at least one diethanolamide of a $C_{12}$-$C_{22}$ fatty acid, wherein (b) potentiates the biocidal activity of (a) to control the growth of at least one microorganism.

2. A biocidal composition according to claim 1, wherein said $C_{12}$-$C_{22}$ fatty acid diethanolamide is an N,N-diethanol tall oil fatty amide; diethanolamides of a mixture of fatty acids comprising iso-oleic acid, oleic acid, palmitic acid and stearic acid; or a mixture thereof.

3. A biocidal composition according to claim 1, wherein said microorganism is selected from algae, fungi, and bacteria.

4. A biocidal composition according to claim 1, wherein said composition is in a liquid form selected from the group consisting of an aqueous solution, dispersion, emulsion or suspension.

5. A biocidal composition according to claim 1, wherein the weight ratio of (a) to (b) ranges from about 99:1 to about 1:99.

6. A biocidal composition according to claim 5, wherein said weight ratio ranges from about 60:10 to about 10:60.

7. A biocidal composition according to claim 6, wherein said weight ratio ranges from about 50:50 to about 25:75.

* * * * *